United States Patent [19]

United States Patent [19]

Walker

[11] 4,123,542
[45] * Oct. 31, 1978

[54] DERIVATIVES OF N-ALKYL IMIDAZOLES
[75] Inventor: Keith A. M. Walker, Palo Alto, Calif.
[73] Assignee: Syntex (U.S.A.) Inc., Palo Alto, Calif.
[*] Notice: The portion of the term of this patent subsequent to Mar. 7, 1995, has been disclaimed.
[21] Appl. No.: 760,804
[22] Filed: Jan. 19, 1977
[51] Int. Cl.² ............... C07D 233/60; A61K 31/415
[52] U.S. Cl. ........................ 424/273 R; 542/413; 548/341
[58] Field of Search ............. 260/309, 240 DJ; 424/273; 548/341

[56] References Cited
U.S. PATENT DOCUMENTS

| 3,658,813 | 4/1972 | Godefroi et al. | 260/309 |
| 3,682,951 | 8/1972 | Kreider | 260/309 |
| 3,717,655 | 2/1973 | Godefroi et al. | 260/309 |
| 3,796,704 | 3/1974 | Metzger et al. | 260/309 |

OTHER PUBLICATIONS

Conant et al., The Chemistry of Organic Compounds, Revised Edition, p. 264, N.Y., MacMillan, 1939.

Primary Examiner—Natalie Trousof
Attorney, Agent, or Firm—Alan M. Krubiner; Gerard A. Blaufarb

[57] ABSTRACT

Compounds of the formula

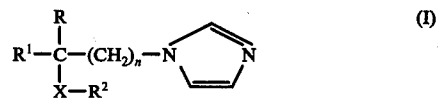

wherein R is lower alkyl; $R^1$ is substituted or unsubstituted phenyl or phenyl straight chain lower alkyl; $R^2$ is substituted or unsubstituted phenyl, phenyl straight chain lower alkyl or phenyl straight chain lower alkenyl; and wherein said substitution, solely in the phenyl ring of the aforesaid groups, comprises one or more substituents independently selected from the group consisting of lower alkyl, lower alkoxy, halo and trifluoromethyl; X is oxygen or sulfur; n is an integer of from 1 to 4 with the proviso that n cannot be 1 when X is oxygen and $R^1$ is phenyl or substituted phenyl; and the antimicrobial acid addition salts thereof are useful as antifungal antibacterial and antiprotozoal agents.

28 Claims, No Drawings

DERIVATIVES OF N-ALKYL IMIDAZOLES

DETAILED DESCRIPTION OF THE INVENTION

The present invention relates to novel chemical compounds which are derivatives of N-alkyl imidazoles. More particularly, the compounds of the present invention are represented by the formula

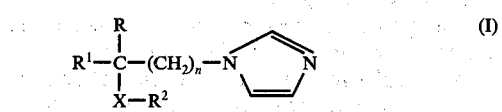

where R is lower alkyl; $R^1$ is substituted or unsubstituted phenyl or phenyl straight chain lower alkyl; $R^2$ is substituted or unsubstituted phenyl, phenyl straight chain lower alkyl or phenyl straight chain lower alkenyl; and wherein said substitution, solely in the phenyl ring of the aforesaid groups, comprises one or more substituents independently selected from the group consisting of lower alkyl, lower alkoxy, halo and trifluoromethyl; X is oxygen or sulfur; n is an integer of from 1 to 4 with the proviso that n cannot be 1 when X is oxygen and $R^1$ is phenyl or substituted phenyl; and the antimicrobial acid addition salts thereof.

In a second aspect the present invention is concerned with a method of combatting fungi, bacteria and protozoa by administering a compound of the present invention or a composition containing same.

As used in the specification and the appended claims, unless specified to the contrary, the following terms have the meaning indicated. The term "lower alkyl" refers to a straight or branched chain monovalent substituent consisting solely of carbon and hydrogen, containing no unsaturation, and having from one to four carbon atoms. Examples of lower alkyl groups are methyl, ethyl, n-propyl, isopropyl, n-butyl, sec-butyl and tert-butyl. The term lower alkoxy refers to a lower alkyl ether substituent wherein the lower alkyl portion is as defined above. The term "lower alkenyl" refers to a straight or branched chain monovalent substituent consisting solely of carbon or hydrogen, containing monoolefinic unsaturation, and having from 3 to 4 carbon atoms. Examples of lower alkenyl groups are prop-1-enyl, prop-2-enyl, but-1-enyl and but-2-enyl. The term cinnamyl refers to the moiety $C_6H_5CH=CH-CH_2-$. The term "halo" refers to fluoro, chloro or bromo. "Antimicrobial acid addition salts" of the subject bases refer to those salts which retain the antimicrobial properties of the free bases and which are neither biologically nor otherwise undesirable, formed with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic aid, mandelic acid, methanesulfonic acid, ethanesulfonic acid, p-toluenesulfonic acid, salicylic acid, and the like. It is also to be understood, for purposes of this invention, that there cannot be 2,3,4- 3,4,5- or 4,5,6- trisubstitution, tetrasubstitution or pentasubstitution in the phenyl rings of $R^1$ and $R^2$ with branched alkyl and/or branched alkoxy and/or trifluoromethyl groups.

All compounds of Formula (I) possess at least one chiral center, i.e., the carbon atom to which are attached the $R^1$, X, $(CH_2)_n$ and R moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds. Additionally, those compounds possessing a substituted or unsubstituted phenyl straight chain lower alkenyl group can have geometric (cis and trans) isomers about the double bond. Both isomers as well as mixtures thereof are intended to be included within the scope of the present invention.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of formula (I) with an optically active acid; or by the separation of the diastereomeric salts or esters formed by reaction of racemic compounds of formula (II), infra, with an optically active acid; or by separation of the diastereomeric esters formed by reaction of alcohols of formula (XVII) with an optically active acid. Exemplary of such optically active acids are the optically active forms of camphor-10-sulfonic acid, α-bromo-camphor-π-sulfonic acid, camphoric acid, menthoxy-acetic acid, tartaric acid, malic acid, diacetyl-tartaric acid, pyrrolidone-5-carboxylic acid, and the like. The separated pure diastereomeric salts or esters may then be cleaved by standard means to afford the respective optical isomers of the compounds of formula (I) or (II).

The subject compounds of formula (I) exhibit anti-fungal, anti-bacterial and anti-protozoal activity. For example, compounds of the present invention exhibit anti-fungal activity against human and animal pathogens such as

*Microsporum audouini,*
Microsporum gypseum,
*Microsporum gypseum — canis,*
*Epidermophyton floccosum,*
*Trichophyton mentagrophytes,*
*Trichophyton rubrum*
*Trichophyton tonsurans*
*Candida albicans,* and
*Cryptococcus neoformans.*

The compounds of the present invention also exhibit anti-fungal activity against the following fungi primarily of agricultural significance *Aspergillus flavus, Aspergillus niger, Cladosporium herbarum, Penicillium oxalicum, Fusarium graminearum, Penicillium spinulosum, Penicillium notatum,* and *Pithomyces chartarum.*

In addition, the compounds of the present invention exhibit anti-bacterial activity against human and animal pathogens, such as

*Staphylococcus aureus,*
*Streptococcus faecalis,*
*Corynebacterium acnes,*
*Erysipelothrix insidiosa,*
*Escherichia coli,*
*Proteus vulgaris,*
*Salmonella choleraesuis,*

*Pasteurella multocida,* and
*Pseudomonas aeruginosa.*

Moreover, the compounds of the present invention exhibit anti-protozoal activity against protozoa such as *Trichomonas vaginalis.*

In general, the subject compounds of the instant invention exhibit a low level of toxicity. Moreover, these compounds demonstrate good solubility in the stratum corneum. Since dermatophyte (i.e., parasitic fungal) infections are usually localized in the dead tissue of the stratum corneum, solubility of anti-fungal agents in this tissue significantly enhances their effectiveness.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semisolid formulations there may be mentioned, for example, poly-alkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emusifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intrasmuscular as well as subcutaneous and intravenous administration. Intravenous injection of imidazole-type anti-fungals has been demonstrated to be effective in the treatment of systemic mycoses (see for example, Drugs, 9, pp. 419–420, 1975, which describes the intravenous administration of miconazole, i.e. 1-[2,4-dichloro-$\beta$-(2',4'-dichlorobenzyloxy)phenethyl]imidazole nitrate, to patients with systemic candidiasis). Topical application is the preferred method of administration for pharmaceutical applications. For such treatment, an area having an existing fungal, bacterial or protozoal growth, or to be protected against attack by fungi, bacteria or protozoa, may be treated with the subject compounds or compositions by, for example, dusting, sprinkling, spraying, rinsing, brushing, dipping, smearing, coating, impregnating and the like. Topical pharmaceutical compositions containing the compounds of the present invention exhibit anti-fungal anti-bacterial and anti-protozoal activity over a wide range of concentration, for example, from about 0.1 to 10.0% by weight of the composition. In any event, the composition to be administered will contain a quantity of the subject compound in an amount effective for relief or prevention of the specific condition being treated.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g., oral or parenteral) administration it is expedient to administer the active ingredient in amounts between about 1 and 100 mg./kg. body weight per day, preferably between about 5 and 50 mg./kg. body weight per day, preferably distributed over several applications (e.g., in 3 individual doses) in order to achieve most effective results. For localized (e.g. topical) administration, however, proportionately less of the active ingredient is required.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

The compounds of formula (I) may be considered to consist of two subclasses, those of formulas (Ia) and (Ib) shown below

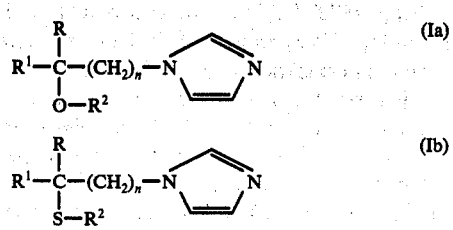

wherein R, $R^1$, $R^2$, and $n$ are as defined above.

Compounds of formula (Ia), and those compounds of formula (Ib) wherein $n > 1$, may be prepared from common intermediates having a free hydroxyl group which is converted to the ether or thioether, as the case may be. The intermediates may be prepared by several methods, depending upon the length of the $(CH_2)_n$ chain, i.e., the value of $n$.

Preferred compounds embraced by generic formula (I) are those wherein $n$ is 1 to 3, $R^1$ is substituted or unsubstituted phenyl, benzyl, phenethyl or phenylpropyl and $R^2$ is substituted or unsubstituted benzyl or phenyl. Within this group the following distinct groups that may be mentioned are those wherein:

a. $R^1$ is substituted or unsubstituted phenyl;
b. $R^1$ is substituted or unsubstituted benzyl; and
c. $R^1$ is substituted or unsubstituted phenethyl or phenylpropyl.

Preferred compounds described in the previous paragraph are those wherein $R^1$ contains halo substitution in the phenyl ring.

Particularly preferred compounds within the group described in subparagraph a) above are those wherein $R^1$ is 4-halo or 2,4-dihalo substituted phenyl, preferably 4-chloro or 2,4-dichloro, and $R^2$ is also substituted benzyl or phenyl wherein said halo substitution preferably includes one halo substituent, preferably chloro, in an ortho or para position.

Particularly preferred compounds within the group described in subparagraph b) above are those compounds wherein $R^1$ is 4-halo or 2,4-dihalo substituted benzyl, preferably 4-chloro or 2,4-dichloro, and $R^2$ is halo substituted benzyl or phenyl wherein said halo substitution preferably includes one halo substituent, preferably chloro, in an ortho or para position.

Particularly preferred compounds within the group described in subparagraph c) above are those wherein $R^1$ is 4-halo or 2,4-dihalo substituted phenethyl or phenylpropyl and $R^2$ is halo and/or methoxy substituted benzyl or phenyl.

Most particularly preferred compounds are those in the group described in the previous paragraph wherein $n$ is 1 and:

a. $R^1$ is 4-halo substituted phenethyl, preferably 4-chloro, and $R^2$ is halo and/or methoxy substituted benzyl or phenyl, preferably phenyl, wherein said substitution preferably includes a substituent in an ortho or para position; and
b. $R^1$ is 2,4-dihalo substituted phenethyl, preferably 2,4-dichloro, and $R^2$ is 4-halo or 4-methoxy subsubstituted benzyl or phenyl, preferably phenyl.

Particularly preferred compounds within all of the aforementioned preferred groups are those wherein X is sulfur and R is methyl.

As mentioned above, compounds of formula (Ia), and those compounds of formula (Ib) wherein $n > 1$, may be prepared by forming an ether or thioether from a suitable alcohol of formula (II)

wherein $R^1$, R and $n$ are as defined above. Compounds of formula (II) may be prepared by several reaction sequences, depending on the size of $n$.

For example, when $n$ is 1, certain compounds of formula (IIa) may be preared by reaction scheme A shown below.

Reaction Scheme A

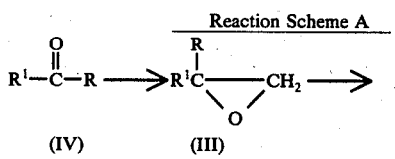

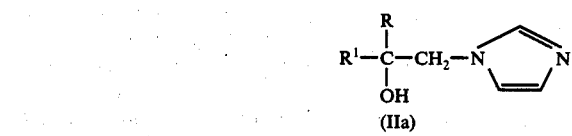

In this reaction scheme the imidazole alcohol of formula (IIa) is formed by opening a terminal epoxide of formula (III) with imidazole. The reaction is preferably carried out in an inert organic solvent using at least one mole of imidazole and optionally 0.05–1 moles of an imidazole salt, e.g. an alkali metal salt, preferable a sodium salt. Suitable solvents that can be used include, for example, dimethylformamide and tetrahydrofuran. The temperature normally employed for such epoxide opening is in the range of from $-20°$ to about $100°$ C., most preferably from about $20°$ to about $60°$ C.

Epoxides of formula (III), insofar as they may not be known or readily available, may be prepared by reaction of a ketone (e.g., (IV)) with the ylide prepared from trimethylsulfoxonium iodide as described, for example, in *J. Am. Chem. Soc.*, 84, p. 867 (1962); ibid, 87, p. 1353 (1965).

Another reaction scheme for preparing certain compounds of formula (IIa) is shown in reaction scheme B presented below Reaction Scheme B

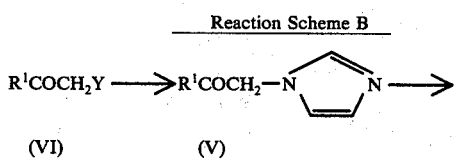

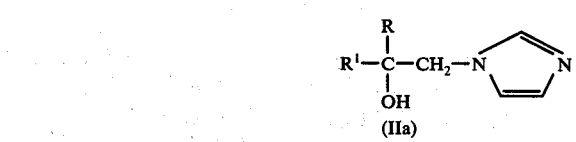

wherein Y is chloro or bromo.

In this reaction scheme the imidazole alcohol of formula (IIa) is prepared by reaction of an organometallic compound with a ketone (V), which in turn is prepared by reaction of an α-halo ketone (VI) with imidazole.

α-Halo ketones are generally available, or may be readily prepared by, for example, halogenation of the corresponding methyl ketone; halogenation of an enol ether or enol ester; treatment of a diazoketone with HX (X=Cl; Br); reaction of a Grignard reagent with chloroacetyl chloride; or reaction of a 1-haloacetylene with mercuric oxide and boron trifluoride followed by treatment with acid.

The α-halo ketone is contacted with imidazole in an inert organic solvent to afford the keto imidazole of formula (V). The reaction is carried out utilizing at least a molar amount and, preferably, an excess of imidazole relative to halo ketone. The reaction may be carried out in the absence of solvent or, preferably, in an inert organic solvent such as for example dimethylformamide, hexamethylphosphoramide, acetonitrile, and the like. The reaction is suitably carried out at a temperature initially between about −10° and 100° C., preferably between about 0° and 25° C.

The conversion of the keto imidazole of formula (V) to the hydroxy imidazole of formula (IIa) is effected by contacting the keto imidazole with an organometallic compound such as an organolithium compound or a Grignard reagent having the desired R moiety. The reaction is conveniently carried out in an inert organic solvent at a temperature between −78° C. and reflux, preferably about −78° C. to 35° C. utilizing at least a molar amount of organo-metallic compound relative to keto imidazole. Suitable inert organic solvents which can be used include, for example, dialkyl ethers (e.g., diethyl ether), tetrahydrofuran and diethers of mono-, di- and triethylene glycols. Hydrocarbons can also be used as cosolvents and solvents. When a Grignard reagent is used in a hydrocarbon solvent, a tertiary amine may optionally be added.

When $n$ is 2, compounds of formula (IIb) may be prepared according to a variety of synthetic methods. One convenient method for the preparation of certain compounds of formula (IIb) is shown in reaction scheme C presented below.

Reaction Scheme C

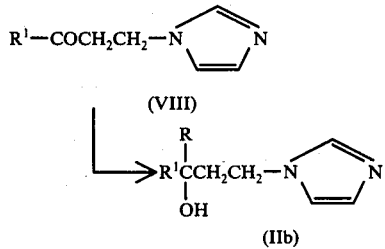

(or Mannich base quaternary salt)
(VII)

(VIII)

(IIb)

This scheme involves the reaction of imidazole with a vinyl ketone of formula (VII) (or Mannich base quaternary intermediate) followed by conversion of the resulting keto imidazole of formula (VIII) to the hydroxy imidazole of formula (IIb).

Vinyl ketones of formula (VII), insofar as they may not be known or generally available, may be prepared by a variety of methods well known in the synthetic organic chemistry art, for example, by the addition of vinyl lithium to the corresponding carboxylic acid; by the addition of vinyl lithium to the corresponding aldehyde followed by oxidation of the allylic alcohol thus produced to the vinyl ketone (e.g., J. Chem. Soc. (C), 1966, p. 1972; J. Chem. Soc. (London), 1956, p. 3070); or by Mannich reaction of the corresponding methyl ketone, quaternization and elimination.

The first step of the conversion, the reaction of vinyl ketone of formula (VII) to keto imidazole of formula (VIII), is accomplished by contacting the vinyl ketone (or a Mannich quaternary base precursor) with imidazole in an inert organic solvent. The reaction is conveniently carried out utilizing at least a molar amount, and preferably an excess, of imidazole relative to vinyl ketone or Mannich quaternary base in an inert organic solvent, for example, diethyl ether, dichloromethane or dimethylformamide, at a temperature between about 0° and 40° C. preferably about ambient temperature.

The conversion of the keto imidazole of formula (VIII) to the hydroxy imidazole of formula (IIb) is carried out in the same manner as described above for the conversion of the compound of formula (V) to that of formula (IIa).

When $n$ is 2 (or greater), certain compounds of formula (II) are conveniently prepared as illustrated in reaction scheme D presented below Reaction Scheme D

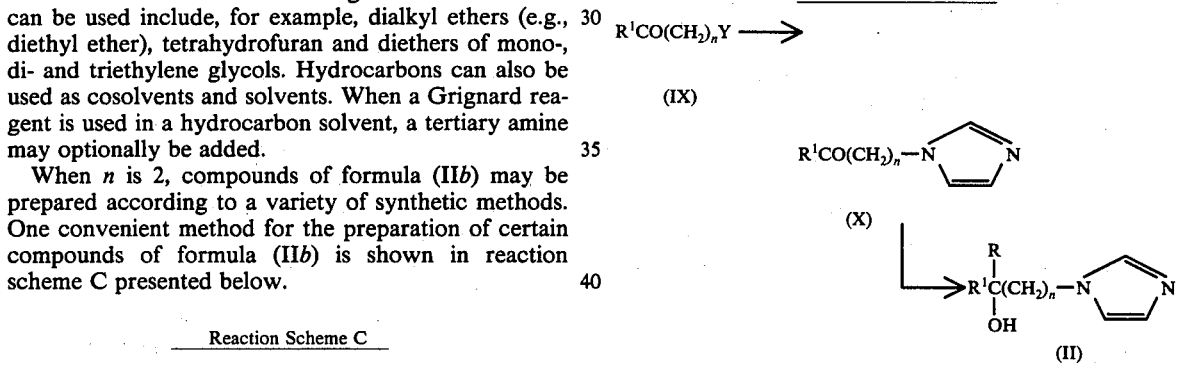

(IX)

(X)

(II)

wherein Y is chloro or bromo.

In this reaction scheme an ω-halo (preferably chloro) ketone of formula (IX) is converted to the corresponding keto imidazole of formula (X) and then to the hydroxy imidazole of the formula (II).

The starting ω-halo ketones, insofar as they may not be known or generally available, may be suitably prepared by the well-known Friedel-Crafts reaction involving the aromatic hydrocarbon $R^1H$ and an ω-halo acylhalide.

The conversion from compound (IX) to compound (X) is carried out using imidazole in the same manner as described above for the conversion of (VI) → (V). When $n$ is 3 or greater, the reaction temperature is between about 0° and 100° C., preferably between 25° and 80° C.

The conversion of the keto imidazole of formula (X) to the hydroxy imidazole of formula (II) is carried out as previously described for the conversion of (V) → (IIa).

Certain compounds of formula (IIc) may also be prepared by an alternate procedure depicted in reaction scheme E

Reaction Scheme E

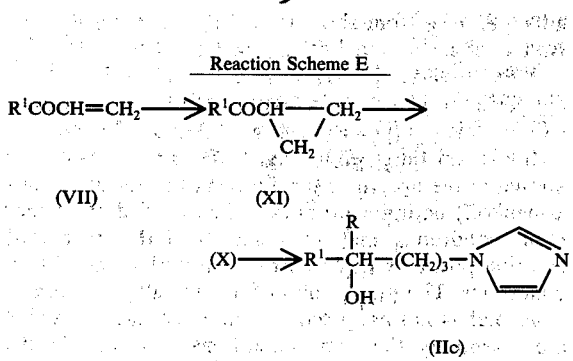

involving the conversion of the previously described vinyl ketone of formula (VII) to the corresponding cyclopropyl ketone of the formula (XI), followed by conversion to the γ-halo ketone of formula (IX), $n=3$, and then, as described above, to the hydroxy imidazole of formula (IIc).

The cyclopropanation of the vinyl ketone of formula (VII) may be accomplished by methods known per se, for example as disclosed in *J. Am. Chem. Soc.*, 87, p. 1353 (1965). The resulting cyclopropyl ketone is then opened to afford the γ-halo ketone by treatment with a hydrohalic acid such as, for example, hydrobromic acid.

Certain compounds of formula (II) may be also prepared as demonstrated below in reaction scheme F.

Reaction Scheme F

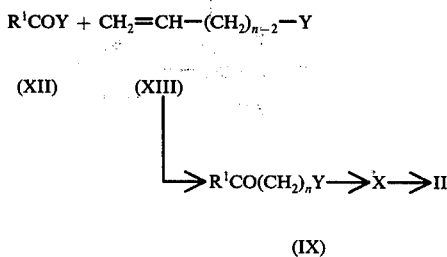

wherein Y is chloro or bromo.

This reaction scheme is conveniently utilized where compounds having n equal to 4 are desired.

In this reaction scheme an acid halide of formula (XII), readily prepared from the corresponding carboxylic acid, is reacted with an ω-halo terminal alkene of formula (XIII), readily prepared, for example, by halogenation of the corresponding alcohol, to afford the halo ketone of the formula (IX), which is then converted, as described above, to the hydroxy imidazole of formula (II). The addition reaction between compounds of formulas (XII) and (XIII) is conveniently carried out under conditions as described in G. Olah, "Friedel Crafts and Related Reactions", Vol. 3, Part 2, Interscience Publishers, New York, (1964), and references therein.

In yet another reaction sequence certain compounds of formula (II) wherein n is 1 or greater may be prepared. This is illustrated below in reaction scheme G.

Reaction Scheme G

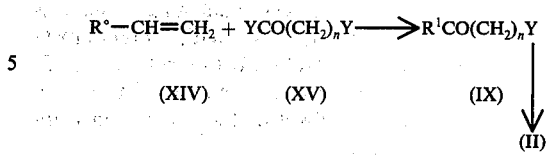

wherein $R^1$ is $R°CH_2CH_2$ and Y is chloro or bromo.

In this scheme the ω-halo ketone of formula (IX), described above, is prepared starting with a terminal olefin of formula (XIV) and an ω-halo acyl halide of formula (XV), readily prepared, for example, from the corresponding hydroxyacid. This reaction is carried out under the conditions described above for reaction scheme F.

The compounds of formula (II) are converted to the final products of formula (I) wherein X is O and $R^2$ is substituted or unsubstituted phenyl straight chain lower alkyl or phenyl straight chain lower alkenyl, by O-alkylation with the appropriate $R^2Y$ wherein Y is a leaving group such as halide (chloride, bromide or iodide) or sulfonate ester (e.g., p-toluenesulfonate or methanesulfonate).

The alkylation is carried out by converting the hydroxy group of the compound of formula (II) to its metal salt, preferably alkali metal salt, by treatment with a strong base such as, for example, an alkali metal hydride such as sodium hydride; an alkali metal amide such as sodium amide or potassium amide; and the like. This is preferably done in an inert organic solvent such as, for example, dimethylformamide, hexamethylphosphoramide, tetrahydrofuran, and the like. The alkali metal salt is then contacted with the $R^2Y$, preferably in the same solvent system, at a temperature between about 0° and 80° C., most preferably between about 0° and 60° C.

Compounds of formula (I) wherein X is O and $R^2$ is phenyl or substituted phenyl may be prepared from compounds of formula (II) by a four-step sequence, e.g., (II) → nitrophenyl ether → amino phenyl ether → diazonium salt → (I).

In the first step in the above sequence, the hydroxy group of the compound of formula (II) is first converted to a metal salt (e.g. an alkali metal salt, preferably a sodium salt) as previously described. The metal salt is then converted to a nitrophenyl ether by contacting it with a halobenzene (preferably a chloro- or fluorobenzene) substituted with at least one nitro group in the ortho and/or para position(s) and optionally containing other substituents. The metal salt is contacted with the nitro substituted halobenzene in the presence of manganese dioxide (if required) and in the same solvent system used to generate the salt. The reaction is suitably carried out at a temperature between about 0° and 100° C. for from 30 minutes to 24 hours.

In the second step in the above sequence, the nitrophenyl ether is reduced to the aminophenyl ether. Reduction is conveniently accomplished by means well known in the art. For example, the nitro group(s) may be reduced using a metal (e.g. Fe, Zn, Sn) and an acid; a salt, such as stannous chloride, and an acid; a metal, such as iron and water; or Fe dust and ammonium chloride (preferred). The reduction may be carried out in water, optionally using an alcohol as a cosolvent, at room temperature to reflux for from 30 minutes to 18 hours.

In the third step in the above sequence, the aminophenyl ether is converted to the corresponding diazonium salt compound by conventional means, such as treatment of the aminophenyl ether with sodium nitrite in a suitable acid at a temperature between 0° and 5° C. (a higher temperature is needed when the $R^2$ moiety of the aminophenyl ether is substituted with electron withdrawing groups).

In the fourth step of the above sequence, the diazonium salt compound is converted to the desired compound of formula (I), wherein X is O and $R^2$ is phenyl or substituted phenyl, by conventional methods. For example, treatment of the diazonium salt compound with cuprous chloride and hydrochloric acid yields a compound of formula (I) wherein the $R^2$ moiety contains chloro substitution; heating a $BF_4^-$ salt yields a compound of formula (I) wherein the $R^2$ moiety contains fluoro substitution; treatment with sulfuric acid and water yields a compound of formula (I) wherein the $R^2$ moiety contains hydroxy substitution (convertible to a lower alkoxy substituent); and treatment with hypophosphorous acid yields a compound of formula I wherein (a) $R^2$ is phenyl (e.g. the $R^2$ moiety of the salt contains only the diazonium group); or (b) $R^2$ is substituted phenyl (e.g. the $R^2$ moiety of the salt contains at least one substituent in addition to the diazonium group).

With reference to the previous paragraph, the substitution in the $R^2$ moiety that results via the diazonium salt occurs at the original point of attachment of the nitro group(s).

Compounds of formula (I) wherein $n$ is 2, 3 or 4, X is S and $R^2$ is substituted or unsubstituted phenyl, phenyl straight chain lower alkyl or phenyl straight chain lower alkenyl may be prepared as depicted in reaction scheme H below a temperature from about 0° to 120° C., preferably between about 20° and 100° C., for from 1 to 48 hours.

Alternatively, the alcohol of formula (II) may be converted to an olefin or mixture of olefins of formula (XVI) which is then reacted with $R^2SH$. The addition of thiols and thiophenols, e.g. $R^2SH$, to olefins is well known in the art and typically results in normal (Markownikoff) addition products when carried out under ionic conditions and abnormal (anti-Markownikoff) addition products when carried out under free radical conditions. The preparation of tertiary alkyl thioethers from olefins normally requires ionic conditions which are essentially the same conditions described in the previous paragraph for the conversion of (II) → (Ib).

Certain olefins of formula XVI may also be prepared from ketones by methods well known in the art, e.g. Wittig reaction on the alcohol precursors of formula (V), (VIII) and (X).

Compounds of formula (I) wherein $n$ is 1, X is S and $R^2$ is substituted or unsubstituted phenyl, phenyl straight chain lower alkyl or phenyl straight chain lower alkenyl are suitably prepared as depicted in reaction scheme I below.

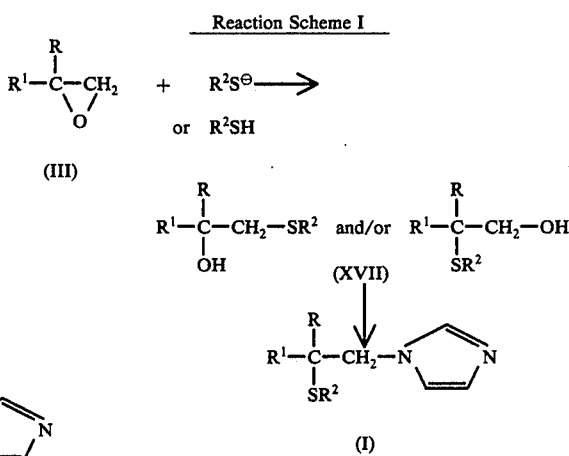

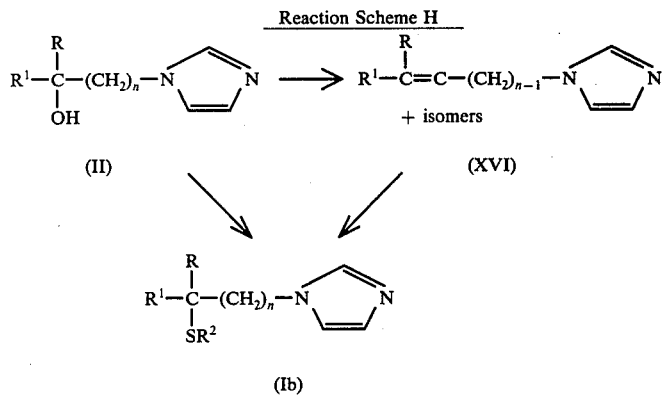

In the above scheme, the tertiary alkyl thioethers of formula (I) are prepared from alcohols of formula (II) or the olefins derived therefrom, by methods well known in the art.

For example, treatment of the alcohol of formula (II) with $R^2SH$ and a suitable acid is productive of compounds of formula (Ib). Suitable acids that may be used include, for example, perchloric acid, sulfuric acid, fluoboric acid, methanesulfonic acid (preferred) and the like. If desired, the acid may be diluted with a cosolvent such as, for example, nitromethane, acetic acid, methylene chloride and the like. Aqueous acids may also be used in the presence of sufficient acetic anhydride to remove the water present. This reaction is carried out at In the first step of the reaction scheme, the epoxide of formula (III) described earlier, is opened with a thiol or thiophenol or a metal salt thereof, to afford the product of formula (XVII) in either or both of the isomeric forms depicted. This portion of the reaction scheme is carried out utilizing a metal salt, preferably an alkali metal salt such as a sodium salt, of the thiol or thiophenol in an inert organic solvent such as, for example, tetrahydrofuran or acetone at a temperature of between about 0° and 67° C., or using the free thiol or thiophenol in the presence of an acid catalyst, e.g., perchloric acid, in an inert solvent such as, for example, methylene chloride, benzene or nitromethane at ambient temperatures or below.

In the next step, the hydroxy group of (XVII) is first converted to a leaving group such as a halide (e.g., chloro or bromo) or sulfonate ester (e.g., p-toluenesulfonate or methanesulfonate) by treatment with, e.g., a halogenating agent such as, for example, thionyl chloride, neat, or preferably in an inert solvent such as dichloromethane, or by treatment with, for example, p-toluenesulfonyl chloride, in an inert solvent in the presence of a base such as pyridine or triethylamine.

Thereafter the halide or sulfonate ester prepared as described above is converted to the final product of formula (I) by treatment with imidazole. This reaction is carried out in an inert organic solvent such as for example acetonitrile, dimethylformamide, and the like, at a temperature of about 0° to about 80° C.

Alternatively, the product of formula (XVII) may be contacted with N,N'-carbonyldiimidazole or N,N'-thionyldiimidazole (preferably N,N'-thionyldiimidazole) in an inert organic solvent to obtain the compounds of formula (I). The reaction is carried out at a temperature between about −20° to 120° C., preferably about 0° to 80° C., utilizing at least a molar amount of reagent relative to the product of formula (XVII). Suitable inert organic solvents that can be used include, for example, tetrahydrofuran, acetonitrile, benzene, toluene, chloroform, methylene dichloride, carbon tetrachloride and the like.

The subject compounds of the instant invention can be isolated as free bases; however, since many of the compounds in base form are oils, it is more convenient to isolate and characterize the compounds as acid addition salts. These salts are prepared in the usual manner, i.e., by reaction of the base compound with a suitable inorganic or organic acid, described above. Salts formed with dibasic acids (e.g., oxalic acid) may generally contain one or two molecules of base per molecule of acid. All oxalates described herein contain one molecule of oxalic acid per molecule of imidazole base. If desired, the salts can be readily converted to the free base form by treatment with alkali, such as potassium carbonate, sodium carbonate or sodium or potassium hydroxide.

The following specific examples are illustrative of the present invention and should not be considered as limitative thereof in any manner.

For the sake of conformity all the compounds recited hereinafter are named in a manner in which the R and $XR^2$ moieties are substituents on the chain bridging $R^1$ and the imidazole ring.

PREPARATION 1

This preparation illustrates the process in reaction scheme A.

4-(4-Chlorophenyl)-2-butanone (42 g.) is added under nitrogen at room temperature to the ylide prepared from trimethylsulfoxonium iodide (60.7 g.) and sodium hydride (12.1 g. of a 50% dispersion in mineral oil) in dry dimethylsulfoxide (300 ml.), according to the procedure in the *Journal of the American Chemical Society*, Vol. 84, page 867 (1962) and Vol. 87, page 1353 (1965). After stirring for 1 hour at room temperature, the reaction mixture is poured into 700 ml of water and the product extracted with ether (2 × 300 ml.). The extract is washed with water, dried (MgSO$_4$) and evaporated to give a colorless oil, 1-[2-(4-chlorophenyl)ethyl]-1-methyloxirane, used directly in the next step. If required in a pure state, the product can be chromatographed on silica gel and eluted with hexane, gradient diluted with up to 30% dichloromethane.

Sodium hydride (6.7 g. of a 50% dispersion in mineral oil) is slowly added to a solution of 13 g. of imidazole in 100 ml. of dry dimethylformamide and the mixture stirred until hydrogen evolution ceases. The resulting suspension is then maintained under nitrogen at room temperature while 25 g. of 2-[2-(4-chlorophenyl)ethyl]-2-methyloxirane (prepared as described above) is added dropwise with stirring.

After stirring overnight, the reaction mixture is poured into a mixture of 1500 ml. of water and 200 ml. of ether. The tan product which precipitates is collected by filtration, washed with water and dried. Recrystallization from benzene yields 26 g. of 1-[2-hydroxy-2-methyl-4-(4-chlorophenyl)-n-butyl]imidazole as white crystals, m.p. 138°–138.5° C.

Similarly, proceeding as above, substituting the appropriate ketone for 4-(4-chlorophenyl)-2-butanone, there may be prepared, for example, the following compounds of formula (IIa):

1-[2-hydroxy-2-methyl-4-(4-fluorophenyl)-n-butyl]imidazole,
1-[2-hydroxy-2-methyl-4-(4-bromophenyl)-n-butyl]imidazole,
1-[2-hydroxy-2-methyl-4-(2,4-dichlorophenyl)-n-butyl]imidazole,
1-[2-hydroxy-2-methyl-4-(2,6-dichlorophenyl)-n-butyl]imidazole,
1-[2-hydroxy-2-methyl-4-phenyl-n-butyl]imidazole,
1-[2-hydroxy-2-methyl-4-(4-methylphenyl)-n-butyl]imidazole,
1-[2-hydroxy-2-methyl-4-(2,4-dimethylphenyl)-n-butyl]imidazole,
1-[2-hydroxy-2-methyl-4-(4-trifluoromethylphenyl)-n-butyl]imidazole,
1-[2-hydroxy-2-methyl-4-(4-methoxyphenyl)-n-butyl]imidazole,
1-[2-hydroxy-2-methyl-5-(4-chlorophenyl)-n-pentyl]imidazole,
1-[2-hydroxy-2-methyl-5-(4-fluorophenyl)-n-pentyl]imidazole,
1-[2-hydroxy-2-methyl-5-(2,4-dichlorophenyl)-n-pentyl]imidazole,
1-[2-hydroxy-2-methyl-5-(4-methylphenyl)-n-pentyl]imidazole,
1-[2-hydroxy-2-methyl-5-(4-methoxyphenyl)-n-pentyl]imidazole,
1-[2-hydroxy-2-methyl-5-(4-ethoxyphenyl)-n-pentyl]imidazole,
1-[2-hydroxy-2-ethyl-4-(4-chlorophenyl)-n-butyl]imidazole,
1-[2-hydroxy-2-n-propyl-4-(4-chlorophenyl)-n-butyl]imidazole,
1-[2-hydroxy-2-n-propyl-4-(4-fluorophenyl)-n-butyl]imidazole,
1-[2-hydroxy-2-n-butyl-4-(4-chlorophenyl)-n-butyl]imidazole,
1-[2-hydroxy-2-n-butyl-4-(4-fluorophenyl)-n-butyl]imidazole, and
1-[2-hydroxy-2-methyl-4-(2-chlorophenyl)-n-butyl]imidazole.

PREPARATION 2

This preparation illustrates the processes of reaction scheme D.

A. 1-(4-Chlorophenyl)-5-chloro-3-pentanone (6.95 g.) is added to a well stirred, ice-cooled solution of 10.5 g. of imidazole in 10 ml. of dimethylformamide. The solution is stirred for 8 hours at 0° C. and then poured into 150 ml. of water. The product is collected by filtration and recrystallized from cyclohexane to yield 1-(4-chlorophenyl)-5-(1-imidazolyl)-3-pentanone.

A stirred solution of 5 g. of the above ketone in 150 ml. of dry tetrahydrofuran is treated under nitrogen at −50° C. with excess methyl magnesium chloride (12.5 ml. 33M solution in ether). Stirring is continued for 1 hour. The mixture is then allowed to come to room temperature and stirred for an additional hour. A saturated ammonium chloride solution is added and the mixture is extracted with ether. Any product, which separates out at this point is collected by filtration and washed with water and then with ether. The combined ethereal solutions are then washed with water, dried (MgSO$_4$) and evaporated to yield 1-[3-hydroxy-3-methyl-5-(4-chlorophenyl)n-pentyl]imidazole which may be purified by recrystallization from ethyl acetate or by chromatography on silica gel eluting with 10% methanol in dichloromethane.

B. To a 0° C. slurry of 17.5g. of imidazole in12.5ml. of dry dimethylformamide is added 10.0 g. of 4-fluoro-65-chlorobutyrophenone and the mixture is stirred overnight at room temperature, then 1 day at 60° C. The resulting solution is then poured into 400 ml. of water and extracted with ethyl acetate. The combined extracts are washed well with water, dried (MgSO$_4$) and the solvent evaporated to afford 1-[4-(4-fluorophenyl)butan-4-onyl]imidazole, purified by chromatography on silica gel eluting with 5% methanol in dichloromethane.

The above ketone is then treated in the manner described above (see A. second paragraph) to afford 1-[4-hydroxy-4-methyl-4-(4-fluorophenyl)-n-butyl-]imidazole.

Similarly, proceeding as above, using the appropriate halo ketones and Grignard reagents for those indicated in part A or B, there may be prepared, for example, all of the compounds of formula (IIa) listed in Preparation 1, as well as the following compounds of formula (II):

1-[3-hydroxy-3-methyl-5-(4-fluorophenyl)-n-pentyl-]imidazole,
1-[3-hydroxy-3-methyl-4-(4-chlorophenyl)-n-butyl-]imidazole,
1-[3-hydroxy-3-methyl-4-(4-fluorophenyl)-n-butyl-]imidazole,
1-[3-hydroxy-3-methyl-4-(4-methoxyphenyl)-n-butyl-]imidazole,
1-[4-hydroxy-4-ethyl-4-(4-chlorophenyl)-n-butyl-]imidazole, and
1-[4-hydroxy-4-n-propyl-5-(4-chlorophenyl)-n-pentyl-]imidazole.

EXAMPLE 1

A solution of 1.2 g. of 1-[2-hydroxy-2-methyl-4-(4-chlorophenyl)-n-butyl]imidazole in 20 ml. of dry hexamethylphosphoramide is treated under nitrogen at about 5° C. with 0.26 g. of a 50% dispersion of sodium hydride in mineral oil. The reaction mixture is stirred at room temperature for 1 hour and then at 60° C. for about 2 hours. After the evolution of hydrogen ceases, the solution is cooled in an ice bath and a solution of 0.88 g. of α,2,4-trichlorotoluene in 10 ml. of dry hexamethylphosphoramide is added dropwise keeping the temperature below 10° C. The solution is then stirred for 1 hour at room temperature and then at 50° C. overnight. The resulting mixture is poured into 500 ml. of water and the aqueous mixture extracted with ether (3 × 100 ml.). The combined extracts are dried (MgSO$_4$) and evaporated. The crude oily product, 1-[2-(4-chlorobenzyloxy)-2-methyl-4-(4-chlorophenyl)-n-butyl]imidazole, is chromatographed on silica gel, eluting with methylene chloride gradient diluted with up to 10% acetone. The pure product is converted to its nitrate salt by treatment of an ethereal solution with concentrated nitric acid. The salt is recrystallized from acetone to yield 1-[2-(2,4-dichlorobenzyloxy)-2-methyl-4-(4-chlorophenyl)-n-butyl]imidazole nitrate, m.p. 148°–149.5° C.

EXAMPLE 2

1-[2-Hydroxy-2-methyl-4-(4-chlorophenyl)-n-butyl-]imidazole (2.60 g.) in 15 ml. of anhydrous dimethylformamide and 7.5 ml. of benzene is treated with 1.12 g. of a 50% dispersion of sodium hydride in mineral oil at room temperature under nitrogen. The mixture is stirred until the evolution of hydrogen ceases and then cooled in ice and treated with 900 mg. of manganese dioxide followed by 2.55 g. of 1-fluoro-4-nitrobenzene. After stirring for 3–4 hours at room temperature, the mixture is poured into 150 ml. of water, extracted with ether and the combined extracts washed with water, dried (MgSO$_4$) and evaporated to yield 1-[2-(4-nitrophenoxy)-2-methyl-4-(4-chlorophenyl)-n-butyl-]imidazole which may be purified, if necessary, by chromatography on silica gel eluting with 5–10% methanol in methylene chloride.

The above obtained 4-nitrophenyl ether (2.0 g.) is added to a mixture of 1.32 g. of iron powder and 1.04 g. of ammonium chloride in 15 ml. of water. The mixture is refluxed for 10 hours and then cooled and extracted with ethyl acetate. The combined extracts are filtered (to remove solids), washed and then dried (MgSO$_4$) and evaporated to afford 1-[2-(4-aminophenoxy)-2-methyl-4-(4-chlorophenyl)-n-butyl]imidazole which is purified by chromatography on silica gel eluting with 10% methanol in dichloromethane.

The above obtained 4-aminophenyl ether (1.2 g.) in a mixture of 7.5 ml. of concentrated hydrochloric acid and 7.5 ml. of water is cooled to about 2° C. and treated dropwise, with stirring with 233 mg. of sodium nitrite in 1.5 ml. of water while the temperature is maintained below 5° C. After the addition is complete, the solution is stirred for approximately 5 minutes at 2°–5° C. and then added, with stirring, to a solution of 420 mg. of cuprous chloride in 15 ml. of concentrated hydrochloric acid at −10° C. The mixture is slowly allowed to come to room temperature with stirring until the evolution of nitrogen ceases. The mixture is then basified with aqueous potassium carbonate solution, shaken with ether, filtered to remove solids and the product extracted with ether. The extracts are then washed with water, dried (MgSO$_4$) and evaporated to afford 1-[2-(4-chlorophenoxy)-2-methyl-4-(4-chlorophenyl)-n-butyl-]imidazole which is purified by chromatography on silica gel eluting with 5% methanol in dichloromethane.

The nitrate salt, prepared by the dropwise addition of concentrated nitric acid to a solution of the product in ether, is recrystallized from acetone/ethyl acetate as snow-white microcrystals.

Similarly, by making appropriate changes in the procedure in paragraph above, e.g. by replacing HCl/CuCl₂ with HBr/CuBr, affords 1-[2-(4-bromophenoxy)-2-methyl-4-(4-chlorophenyl)-n-butyl]imidazole.

EXAMPLE 3

1-[3-Hydroxy-3-methyl-5-(4-chlorophenyl)-n-pentyl]imidazole (1.0 g.) in 2 ml. of methanesulfonic acid is treated with excess 4-chlorothiophenol (1.0 g.) and the mixture is stirred at 70°–80° C. for 3–4 hours. The resulting solution is transferred to a mixture of dilute aqueous potassium carbonate and ether and the basified product then extracted with ether. The extracts are washed with water and dried (MgSO₄). The product, 1-[3-(4-chlorophenylthio)-3-methyl-5-(4-chlorophenyl)-n-pentyl]imidazole, is precipitated as the nitrate salt by the dropwise addition of concentrated nitric acid (d=1.4) to the ether solution. Recrystallization of the salt from acetone/ethyl acetate gives snow-white microcrystals.

EXAMPLE 4

4-Chlorobenzylthiol (2.38 g.) is added to a stirred mixture of 0.52 g. of sodium hydride (50% dispersion in mineral oil) in 20 ml. of dry tetrahydrofuran and stirring (under nitrogen) is continued at room temperature for 1 hour. Thereafter, 1.96 g. of 2-[2-(4-chlorophenyl)ethyl]-2-methyloxirane is added and the mixture is stirred for an additional 4 hours at room temperature and then at 50° C. for 1 hour. The solvent is then removed, 50 ml. of water is added to the residue, and the product is extracted with ethyl acetate (3 × 50). The combined extracts are washed with water, dried (MgSO₄) and evaporated to give an oil.

The above obtained oil is added to 2 ml. of thionyl chloride in 30 ml. of methylene chloride and stirring is maintained overnight. The solution is then evaporated to dryness and the resulting orange oil dissolved in 30 ml. of acetonitrile. Imidazole (4.08 g.) is then added and the mixture is stirred at room temperature for 4 hours and then at 80° C. over the weekend. The solvent is allowed to boil off at 100° C. and water is added to the residue. The aqueous mixture is extracted three times with ethyl acetate. The combined extracts are dried (MgSO₄) and evaporated. The resulting crude oil is purified by chromatography on silica gel eluting with methylene chloride → 15% acetone in methylene chloride. The product, 1-[2-(4-chlorobenzylthio)-2-methyl-4-(4-chlorophenyl)-n-butyl]imidazole, is precipitated as the nitrate salt by the dropwise addition of concentrated nitric acid (d=1.4) to the free base in ether. Recrystallization of the salt from ethyl acetate/ethanol gives a while solid (0.8 g.), m.p. 141°–146° C.

EXAMPLE 5

A mixture of 4 g. of 2-[2-(4-chlorophenyl)ethyl]-2-methyloxirane, 3.6 g. of 2-chlorothiophenol and 500 mg. of anhydrous potassium carbonate in 50 ml. of acetone is stirred at reflux for approximately 3 hours. The solvent is then evaporated and 200 ml. of ether is added to the residue. The resulting mixture is washed with water (3 × 40 ml.), dried (MgSO₄) and evaporated to afford 4-(4-chlorophenyl)-1-(2-chlorophenylthio)-2-methyl-2-butanol which is used directly as described later in the procedure.

Thionyl chloride (2.92 ml.) is added dropwise to a stirred ice-cooled mixture of 10.9 g. of imidazole in about 140 ml. of dry tetrahydrofuran. After addition is complete the cooling bath is removed. The mixture is then stirred for about 1 hour at room temperature and then cooled in an ice bath and the product, N,N'-thionyldiimidazole, filtered directly into a flask containined a stirred solution of the alcohol (prepared in the preceding paragraph) in 50 ml. of tetrahydrofuran. The filtered imidazole hydrochloride is then washed with cold tetrahydrofuran and the washings filtered directly into the flask. The solution in the reaction flask is then stirred overnight. After evaporation to dryness the residue is treated with dilute aqueous potassium carbonate and the product extracted with ether. The combined extracts are washed well with water and dried (MgSO₄). The oxalate salt is prepared by the dropwise addition of an ethereal solution of anhydrous oxalic acid until precipitation is complete. The precipitate is allowed to settle and the ether decanted. The resulting residue is crystallized in about 150 ml. of acetate to afford 1.70 g. of the oxalate salt of the desired isomer, i.e. 1-[2-(2-chlorophenylthio)-2-methyl-4-(4-chlorophenyl)-n-butyl]imidazole.

The above obtained oxalate salt is converted to the free base by stirring in a mixture of potassium carbonate solution (50 ml.) and ether (150 ml.) until no solid remains. The ether solution is then evaporated, washed with water, dried (MgSO₄) and treated dropwise with concentrated nitric acid until precipitation is complete. Recrystallization of the precipitate from ethyl/acetate gives 1.22 g. of the nitrate salt of 1-[2-(2-chlorophenylthio)-2-methyl-4-(4-chlorophenyl)-n-butyl]imidazole as snow white granules, m.p. 137.5°–138.5° C.

EXAMPLE 6

A mixture of 2 g. of 2-[2-(4-chlorophenyl)ethyl]-2-methyloxirane, 1.5 g. of 4-chlorothiophenol and 1.4 g. of anhydrous potassium carbonate in 30 ml. of acetone is stirred at reflux overnight. The solvent is then evaporated and the residue extracted with ether. The combined extracts are washed with water, dried (MgSO₄) and evaporated. The resulting residue is stirred with 5 ml. of thionyl chloride at room temperature. After stirring for one hour, excess thionyl chloride is removed under vacuum and 4 g. of imidazole and about 3 ml. of acetonitrile are added. The mixture is then stirred at 100° C. (bath temperature) for 2 days. Thereafter, the solvent is evaporated and 50 ml. of water is added to the residue. The aqueous mixture is extracted with ether, and the combined extracts washed and dried (MgSO₄). After evaporation to dryness, the residue is chromatographed on silica gel eluting with 10% acetone/dichloromethane. Thereafter the oxalate salt of the resulting product (mixture of isomers) is precipitated, crystalized and converted to the nitrate salt of 1-[2-(4-chlorophenylthio)-2-methyl-4-(4-chlorophenyl)-n-butyl]imidazole by the method described in the previous example. The nitrate salt, 540 mg., is obtained as snow white granules, m.p. 174°–175° C. (foaming).

EXAMPLE 7

Following the procedures in Preparations 1 or 2, and Examples 1, 2, 3, 4, 5 or 6 using equivalent amounts of the appropriate starting materials, there may be prepared the following compounds which, where indicated, are further characterized by conversion to the indicated acid addition salt.

1-[2-(3-chlorophenylthio)-2-methyl-4-(4-chlorophenyl)-n-butyl]imidazole,
1-[2-(2,3-dichlorophenylthio)-2-methyl-4-(4-chlorophenyl)-n-butyl]imidazole,
1-[2-(2,4-dichlorophenylthio)-2-methyl-4-(4-chlorophenyl)-n-butyl]imidazole, nitrate salt, m.p. 126.5°-128° C.,
1-[2-(2,5-dichlorophenylthio)-2-methyl-4-(4-chlorophenyl)-n-butyl]imidazole,
1-[2-(2,6-dichlorophenylthio)-2-methyl-4-(4-chlorophenyl)-n-butyl]imidazole, nitrate salt, m.p. 149.5°-150° C.,
1-[2-(3,4-dichlorophenylthio)-2-methyl-4-(4-chlorophenyl)-n-butyl]imidazole,
1-[2-(2,4,6-trichlorophenylthio)-2-methyl-4-(4-chlorophenyl)-n-butyl]imidazole,
1-[2-(2,4,5-trichlorophenylthio)-2-methyl-4-(4-chlorophenyl)-n-butyl]imidazole,
1-[2-(2-bromophenylthio)-2-methyl-4-(4-chlorophenyl)-n-butyl]imidazole,
1-[2-(4-chlorophenylthio)-2-methyl-4-(2-chlorophenyl)-n-butyl]imidazole,
1-[2-(4-bromophenylthio)-2-methyl-4-(4-chlorophenyl)-n-butyl]imidazole,
1-[2-(3-bromophenylthio)-2-methyl-4-(4-chlorophenyl)-n-butyl]imidazole,
1-[2-(2,4-dibromophenylthio)-2-methyl-4-(4-chlorophenyl)-n-butyl]imidazole,
1-[2-(2,5-dibromophenylthio)-2-methyl-4-(4-chlorophenyl)-n-butyl]imidazole,
1-[2-(2,6-dibromophenylthio)-2-methyl-4-(4-chlorophenyl)-n-butyl]imidazole,
1-[2-(2-fluorophenylthio)-2-methyl-4-(4-chlorophenyl)-n-butyl]imidazole,
1-[2-(3-fluorophenylthio)-2-methyl-4-(4-chlorophenyl)-n-butyl]imidazole,
1-[2-(4-fluorophenylthio)-2-methyl-4-(4-chlorophenyl)-n-butyl]imidazole,
1-[2-(2,6-difluorophenylthio)-2-methyl-4-(4-chlorophenyl)-n-butyl]imidazole,
1-[2-(2,4-difluorophenylthio)-2-methyl-4-(4-chlorophenyl)-n-butyl]imidazole,
1-[2-(2-methylphenylthio)-2-methyl-4-(4-chlorophenyl)-n-butyl]imidazole,
1-[2-(4-methylphenylthio)-2-methyl-4-(4-chlorophenyl)-n-butyl]imidazole,
1-[2-(2-ethylphenylthio)-2-methyl-4-(4-chlorophenyl)-n-butyl]imidazole,
1-[2-(2-isopropylphenylthio)-2-methyl-4-(4-chlorophenyl)-n-butyl]imidazole,
1-[2-(2-n-propylphenylthio)-2-methyl-4-(4-chlorophenyl)-n-butyl]imidazole,
1-[2-(2,6-dimethylphenylthio)-2-methyl-4-(4-chlorophenyl)-n-butyl]imidazole,
1-[2-(2,4-dimethylphenylthio)-2-methyl-4-(4-chlorophenyl)-n-butyl]imidazole,
1-[2-(2,5-dimethylphenylthio)-2-methyl-4-(4-chlorophenyl)-n-butyl]imidazole,
1-[2-(2,4,6-trimethylphenylthio)-2-methyl-4-(4-chlorophenyl)-n-butyl]imidazole,
1-[2-(2,3,6-trimethylphenylthio)-2-methyl-4-(4-chlorophenyl)-n-butyl]imidazole,
1-[2-(2,3,5-trimethylphenylthio)-2-methyl-4-(4-chlorophenyl)-n-butyl]imidazole,
1-[2-(3-chloro-4-trifluoromethylphenylthio)-2-methyl-4-(4-chlorophenyl)-n-butyl]imidazole,
1-[2-(2-trifluoromethylphenylthio)-2-methyl-4-(4-chlorophenyl)-n-butyl]imidazole.
1-[2-(4-trifluoromethylphenylthio)-2-methyl-4-(4-chlorophenyl)-n-butyl]imidazole,
1-[2-(2-methoxyphenylthio)-2-methyl-4-(4-chlorophenyl)-n-butyl]imidazole,
1-[2-(3-methoxyphenylthio)-2-methyl-4-(4-chlorophenyl)-n-butyl]imidazole,
1-[2-(4-methoxyphenylthio)-2-methyl-4-(4-chlorophenyl)-n-butyl]imidazole,
1-[2-(2-methoxy-5-chlorophenylthio)-2-methyl-4-(4-chlorophenyl)-n-butyl]imidazole,
1-[2-(2-chloro-5-methoxyphenylthio)-2-methyl-4-(4-chlorophenyl)-n-butyl]imidazole,
1-[2-(2,6-dimethoxyphenylthio)-2-methyl-4-(4-chlorophenyl)-n-butyl]imidazole,
1-[2-(2,3-dimethoxyphenylthio)-2-methyl-4-(4-chlorophenyl)-n-butyl]imidazole,
1-[2-(2-isopropoxyphenylthio)-2-methyl-4-(4-chlorophenyl)-n-butyl]imidazole,
1-[2-(2-ethoxyphenylthio)-2-methyl-4-(4-chlorophenyl)-n-butyl]imidazole,
1-[2-(4-n-butoxyphenylthio)-2-methyl-4-(4-chlorophenyl)-n-butyl]imidazole,
1-[2-(2-chlorophenylthio)-2-methyl-4-(4-fluorophenyl)-n-butyl]imidazole,
1-[2-(3-chlorophenylthio)-2-methyl-4-(4-fluorophenyl)-n-butyl]imidazole,
1-[2-(4-chlorophenylthio)-2-methyl-4-(4-fluorophenyl)-n-butyl]imidazole,
1-[2-(2,3-dichlorophenylthio)-2-methyl-4-(4-fluorophenyl)-n-butyl]imidazole,
1-[2-(2,4-dichlorophenylthio)-2-methyl-4-(4-fluorophenyl)-n-butyl]imidazole, nitrate salt, m.p. 131°-131.5° C. (foaming),
1-[2-(2,5-dichlorophenylthio)-2-methyl-4-(4-fluorophenyl)-n-butyl]imidazole,
1-[2-(2,6-dichlorophenylthio)-2-methyl-4-(4-fluorophenyl)-n-butyl]imidazole, nitrate salt, m.p. 147.5°-148° C.,
1-[2-(3,4-dichlorophenylthio)-2-methyl-4-(4-fluorophenyl)-n-butyl]imidazole,
1-[2-(2,3,4-trichlorophenylthio)-2-methyl-4-(4-fluorophenyl)-n-butyl]imidazole,
1-[2-(2,3,5-trichlorophenylthio)-2-methyl-4-(4-fluorophenyl)-n-butyl]imidazole,
1-[2-(2,3,6-trichlorophenylthio)-2-methyl-4-(4-fluorophenyl)-n-butyl]imidazole,
1-[2-(2,4,6-trichlorophenylthio)-2-methyl-4-(4-fluorophenyl)-n-butyl]imidazole,
1-[2-(2,4,5-trichlorophenylthio)-2-methyl-4-(4-fluorophenyl)-n-butyl]imidazole,
1-[2-(2-bromophenylthio)-2-methyl-4-(4-fluorophenyl)-n-butyl]imidazole,
1-[2-(4-bromophenylthio)-2-methyl-4-(4-fluorophenyl)-n-butyl]imidazole,
1-[2-(3-bromophenylthio)-2-methyl-4-(4-fluorophenyl)-n-butyl]imidazole,
1-[2-(2,4-dibromophenylthio)-2-methyl-4-(4-fluorophenyl)-n-butyl]imidazole,
1-[2-(2,5-dibromophenylthio)-2-methyl-4-(4-fluorophenyl)-n-butyl]imidazole,
1-[2-(2,6-dibromophenylthio)-2-methyl-4-(4-fluorophenyl)-n-butyl]imidazole,
1-[2-(2-fluorophenylthio)-2-methyl-4-(4-fluorophenyl)-n-butyl]imidazole,
1-[2-(3-fluorophenylthio)-2-methyl-4-(4-fluorophenyl)-n-butyl]imidazole, 1-[2-(4-fluorophenylthio)-2-methyl-4-(4-fluorophenyl)-n-butyl]imidazole,
1-[2-(2,6-difluorophenylthio)-2-methyl-4-(4-fluorophenyl)-n-butyl]imidazole,
1-[2-(2,4-difluorophenylthio)-2-methyl-4-(4-fluorophenyl)-n-butyl]imidazole,
1-[2-(2-methylphenylthio)-2-methyl-4-(4-fluorophenyl)-n-butyl]imidazole,
1-[2-(4-methylphenylthio)-2-methyl-4-(4-fluorophenyl)-n-butyl]imidazole,
1-[2-(2-ethylphenylthio)-2-methyl-4-(4-fluorophenyl)-n-butyl]imidazole,
1-[2-(2-isopropylphenylthio)-2-methyl-4-(4-fluorophenyl)-n-butyl]imidazole,
1-[2-(2-n-propylphenylthio)-2-methyl-4-(4-fluorophenyl)-n-butyl]imidazole,
1-[2-(4-tert-butylphenylthio)-2-methyl-4-(4-fluorophenyl)-n-butyl]imidazole,
1-[2-(2,6-dimethylphenylthio)-2-methyl-4-(4-fluorophenyl)-n-butyl]imidazole,
1-[2-(2,4-dimethylphenylthio)-2-methyl-4-(4-fluorophenyl)-n-butyl]imidazole,
1-[2-(2,5-dimethylphenylthio)-2-methyl-4-(4-fluorophenyl)-n-butyl]imidazole,
1-[2-(2,4,6-trimethylphenylthio)-2-methyl-4-(4-fluorophenyl)-n-butyl]imidazole,
1-[2-(2,3,6-trimethylphenylthio)-2-methyl-4-(4-fluorophenyl)-n-butyl]imidazole,
1-[2-(2,3,5-trimethylphenylthio)-2-methyl-4-(4-fluorophenyl)-n-butyl]imidazole,
1-[2-(3-chloro-4-trifluoromethylphenylthio)-2-methyl-4-(4-fluorophenyl)-n-butyl]imidazole,
1-[2-(2-trifluoromethylphenylthio)-2-methyl-4-(4-fluorophenyl)-n-butyl]imidazole,
1-[2-(4-trifluoromethylphenylthio)-2-methyl-4-(4-fluorophenyl)-n-butyl]imidazole,
1-[2-(2-methoxy-5-chlorophenylthio)-2-methyl-4-(4-fluorophenyl)-n-butyl]imidazole,
1-[2-(2-chloro-5-methoxyphenylthio)-2-methyl-4-(4-fluorophenyl)-n-butyl]imidazole,
1-[2-(2-isopropoxyphenylthio)-2-methyl-4-(4-fluorophenyl)-n-butyl]imidazole,
1-[2-(2-ethoxyphenylthio)-2-methyl-4-(4-fluorophenyl)-n-butyl]imidazole,
1-[2-(3-n-butylphenylthio)-2-methyl-4-(4-fluorophenyl)-n-butyl]imidazole,
1-[2-(4-n-butoxyphenylthio)-2-methyl-4-(4-fluorophenyl)-n-butyl]imidazole,
1-[2-(2-chlorophenylthio)-2-methyl-4-(4-bromophenyl)-n-butyl]imidazole,
1-[2-(3-chlorophenylthio)-2-methyl-4-(4-bromophenyl)-n-butyl]imidazole,
1-[2-(4-chlorophenylthio)-2-methyl-4-(4-bromophenyl)-n-butyl]imidazole,
1-[2-(2,4-dichlorophenylthio)-2-methyl-4-(4-bromophenyl)-n-butyl]imidazole,
1-[2-(2,5-dichlorophenylthio)-2-methyl-4-(4-bromophenyl)-n-butyl]imidazole,
1-[2-(2,6-dichlorophenylthio)-2-methyl-4-(4-bromophenyl)-n-butyl]imidazole,
1-[2-(2-bromophenylthio)-2-methyl-4-(4-bromophenyl)-n-butyl]imidazole,
1-[2-(4-bromophenylthio)-2-methyl-4-(4-bromophenyl)-n-butyl]imidazole,
1-[2-(2,4-dibromophenylthio)-2-methyl-4-(4-bromophenyl)-n-butyl]imidazole,
1-[2-(2,5-dibromophenylthio)-2-methyl-4-(4-bromophenyl)-n-butyl]imidazole,
1-(2-(2,6-dibromophenylthio)-2-methyl-4-(4-bromophenyl)-n-butyl]imidazole,
1-[2-(2-fluorophenylthio)-2-methyl-4-(4-bromophenyl)-n-butyl]imidazole,
1-[2-(2-methylphenylthio)-2-methyl-4-(4-bromophenyl)-n-butyl]imidazole,
1-[2-(4-methylphenylthio)-2-methyl-4-(4-bromophenyl)-n-butyl]imidazole,
1-[2-(2,6-dimethylphenylthio)-2-methyl-4-(4-bromophenyl)-n-butyl]imidazole,
1-[2-(4-chlorophenylthio)-2-methyl-4-(2,4-dichlorophenyl)-n-butyl]imidazole, nitrate salt, m.p. 150°–153° C.,
1-[2-(4-bromophenylthio)-2-methyl-4-dichlorophenyl)-n-butyl]imidazole,
1-[2-(4-fluorophenylthio)-2-methyl-4-(2,4-dichlorophenyl)-n-butyl]imidazole,
1-[2-(4-methylphenylthio)-2-methyl-4-(2,4-dichlorophenyl)-n-butyl]imidazole,
1-[2-(4-ethylphenylthio)-2-methyl-4-(2,4-dichlorophenyl)-n-butyl]imidazole,
1-[2-(4-methoxyphenylthio)-2-methyl-4-(2,4-dichlorophenyl)-n-butyl]imidazole,
1-[2-(4-ethoxyphenylthio)-2-methyl-4-(2,4-dichlorophenyl)-n-butyl]imidazole,
1-[2-(4-isopropoxyphenylthio)-2-methyl-4-(2,4-dichlorophenyl)-n-butyl]imidazole,
1-[2-(4-n-propoxyphenylthio)-2-methyl-4-(2,4-dichlorophenyl)-n-butyl]imidazole,
1-[2-(2-chlorophenylthio)-2-methyl-5-(4-chlorophenyl)-n-pentyl]imidazole,
1-[2-(4-chlorophenylthio)-2-methyl-5-(4-chlorophenyl)-n-pentyl]imidazole,
1-[2-(2,4-dichlorophenylthio)-2-methyl-5-(4-chlorophenyl)-n-pentyl]imidazole,
1-[2-(2,5-dichlorophenylthio)-2-methyl-5-(4-chlorophenyl)-n-pentyl]imidazole,
1-[2-(2,6-dichlorophenylthio)-2-methyl-5-5-(4-chlorophenyl)-n-pentyl]imidazole,
1-[2-(2-bromophenylthio)-2-methyl-5-(4-chlorophenyl)-n-pentyl]imidazole,
1-[2-(2-methylphenylthio)-2-methyl-5-(4-chlorophenyl)-n-pentyl]imidazole,
1-[2-(2-methoxyphenylthio)-2-methyl-5-(4-chlorophenyl)-n-pentyl]imidazole,
1-[2-(2-chlorophenylthio)-2-methyl-5-(4-fluorophenyl)-n-pentyl]imidazole,
1-[2-(4-chlorophenylthio)-2-methyl-5-(4-fluorophenyl)-n-pentyl]imidazole,
1-(2-(2,6-dichlorophenylthio)-2-methyl-5-(4-fluorophenyl)-n-pentyl]imidazole,
1-[2-(2,6-dichlorophenylthio)-2-methyl-4-(4-methoxyphenyl)-n-butyl]imidazole,
1-[2-(2,5-dichlorophenylthio)-2-methyl-4-(4-methoxyphenyl)-n-butyl]imidazole,
1-[2-(2,4-dichlorophenylthio)-2-methyl-4-phenyl-n-butyl]imidazole
1-[2-(2,6-dichlorophenylthio)-2-methyl-4-(4-methylphenyl)-n-butyl]imidazole,
1-[2-(4-chlorophenylthio)-2-methyl-4-(2,4-dimethylphenyl)-n-butyl]imidazole,
1-[2-(2-chlorophenylthio)-2-methyl-4-(4-trifluoromethylphenyl)-n-butyl]imidazole,
1-[2-(2-chlorophenylthio)-2-methyl-5-(4-methylphenyl)-n-pentyl]imidazole,
1-[2-(4-methoxyphenyl)-2-methyl-5-(4-methylphenyl)-n-pentyl]imidazole, 1-[2-(4-ethoxyphenyl)-2-methyl-5-(4-methylphenyl)-n-pentyl]imidazole,
1-[2-phenylthio-2-methyl-5-(2,4-dichlorophenyl)-n-pentyl]imidazole,
1-[2-(2-chlorophenylthio)-2-ethyl-4-(4-chlorophenyl)-n-butyl]imidazole,
1-[2-(4-chlorophenylthio)-2-ethyl-4-(4-chlorophenyl)-n-butyl]imidazole,
1-[2-(2,4-dichlorophenylthio)-2-ethyl-4-(4-chlorophenyl)-n-butyl]imidazole,
1-[2-(2,5-dichlorophenylthio)-2-ethyl-4-(4-chlorophenyl)-n-butyl]imidazole,
1-[2-(2,6-dichlorophenylthio)-2-ethyl-4-(4-chlorophenyl)-n-butyl]imidazole,
1-[2-(2-bromophenylthio)-2-ethyl-4-(4-chlorophenyl)-n-butyl]imidazole,
1-[2-(4-bromophenylthio)-2-ethyl-4-(4-chlorophenyl)-n-butyl]imidazole,
1-[2-(2-fluorophenylthio)-2-ethyl-4-(4-chlorophenyl)-n-butyl]imidazole,
1-[2-(4-fluorophenylthio)-2-ethyl-4-(4-chlorophenyl)-n-butyl]imidazole,
1-[2-(2-methylphenylthio)-2-ethyl-4-(4-chlorophenyl)-n-butyl]imidazole,
1-[2-(2-chlorophenylthio)-2-n-propyl-4-(4-chlorophenyl)-n-butyl]imidazole,
1-[2-(4-chlorophenylthio)-2-n-propyl-4-(4-chlorophenyl)-n-butyl]imidazole,
1-[2-(2,6-dichlorophenylthio)-2-n-propyl-4-(4-chlorophenyl)-n-butyl]imidazole,
1-[2-bromophenylthio)-2-n-propyl-4-(4-chlorophenyl)-n-butyl]imidazole,
1-[2-fluorophenylthio)-2-n-propyl-4-(4-chlorophenyl)-n-butyl]imidazole,
1-[2-(4-fluorophenylthio)-2-n-propyl-4-(4-chlorophenyl)-n-butyl]imidazole,
1-[2-(2-methylphenylthio)-2-n-propyl-4-(4-chlorophenyl)-n-butyl]imidazole,
1-[2-(2-chlorophenylthio)-2-n-propyl-4-(4-fluorophenyl)-n-butyl]imidazole,
1-[2-(2-chlorophenylthio)-2-n-butyl-4-(4-chlorophenyl)-n-butyl]imidazole,
1-[2-(4-chlorophenylthio)-2-n-butyl-4-(4-chlorophenyl)-n-butyl]imidazole,
1-[2-(2,6-dichlorophenylthio)-2-n-butyl-4-(4-chlorophenyl)-n-butyl]imidazole,
1-[2-(2-fluorophenylthio)-2-n-butyl-4-(4-chlorophenyl)-n-butyl]imidazole,
1-[2-(4-fluorophenylthio)-2-n-butyl-4-(4-chlorophenyl)-n-butyl]imidazole,
1-[2-(2-methylphenylthio)-2-n-butyl-4-(4-chlorophenyl)-n-butyl]imidazole,
1-[2-(4-chlorophenylthio)-2-tert-butyl-4-(4-fluorophenyl)-n-butyl]imidazole,
1-[2-(4-chlorobenzylthio)-2-methyl-4-(4-chlorophenyl)-n-butyl]imidazole, nitrate salt, m.p. 141°–146° C.,
1-[2-(2-chlorobenzylthio)-2-methyl-4-(4-chlorophenyl)-n-butyl]imidazole,
1-[2-(2,4-dichlorobenzylthio)-2-methyl-4-(4-chlorophenyl)-n-butyl]imidazole, nitrate salt, m.p. 139.5°–144° C.
1-[2-(2-bromobenzylthio)-2-methyl-4-(4-chlorophenyl)-n-butyl]imidazole,
1-[2-(4-bromobenzylthio)-2-methyl-4-(4-chlorophenyl)-n-butyl]imidazole,
1-[2-(2-fluorobenzylthio)-2-methyl-4-(4-chlorophenyl)-n-butyl]imidazole,
1-[2-(4-fluorobenzylthio)-2-methyl-4-(4-chlorophenyl)-n-butyl]imidazole,
1-[2-(4-methoxybenzylthio)-2-methyl-4-(4-chlorophenyl)-n-butyl]imidazole,
1-[2-(4-chlorobenzylthio)-2-methyl-4-(4-fluorophenyl)-n-butyl]imidazole,
1-[2-(2-chlorobenzylthio)-2-methyl-4-(4-fluorophenyl)-n-butyl]imidazole,
1-[2-(2,4-dichlorobenzylthio)-2-methyl-4-(4-fluorophenyl)-n-butyl]imidazole,
1-[2-(2,5-dichlorobenzylthio)-2-methyl-4-(4-fluorophenyl)-n-butyl]imidazole,
1-[2-(2,6-dichlorobenzylthio)-2-methyl-4-(4-fluorophenyl)-n-butyl]imidazole,
1-[2-(3,4-dichlorobenzylthio)-2-methyl-4-(4-fluorophenyl)-n-butyl]imidazole,
1-[2-(2-bromobenzylthio)-2-methyl-4-(4-fluorophenyl)-n-butyl]imidazole,
1-[2-(4-bromobenzylthio)-2-methyl-4-(4-fluorophenyl)-n-butyl]imidazole,
1-[2-(4-chlorobenzylthio)-2-methyl-4-(4-bromophenyl)-n-butyl]imidazole,
1-[2-(2-chlorobenzylthio)-2-methyl-4-(4-bromophenyl)-n-butyl]imidazole,
1-[2-(2-bromobenzylthio)-2-methyl-4-(4-bromophenyl)-n-butyl]imidazole,
1-[2-(4-bromobenzylthio)-2-methyl-4-(4-bromophenyl)-n-butyl]imidazole,
1-[2-(4-fluorobenzylthio)-2-methyl-4-(4-bromophenyl)-n-butyl]imidazole,
1-[2-(2-chlorobenzylthio)-2-methyl-4-phenyl-n-butyl]imidazole,
1-[2-(4-chlorobenzylthio)-2-methyl-4-(4-methylphenyl)-n-butyl]imidazole,
1-[2-(2,4-dichlorobenzylthio)-2-methyl-4-(4-methoxyphenyl)-n-butyl]imidazole,
1-[2-(2-chlorobenzylthio)-2-methyl-5-(4-chlorophenyl)-n-pentyl]imidazole,
1-[2-(4-chlorobenzylthio)-2-methyl-5-(4-chlorophenyl)-n-pentyl]imidazole,
1-[2-(2-methylbenzylthio)-2-methyl-5-(4-chlorophenyl)-n-pentyl]imidazole,
1-[2-(4-methoxybenzylthio)-2-methyl-5-(4-chlorophenyl)-n-pentyl]imidazole,
1-[2-(2-chlorobenzyloxy)-2-methyl-4-(4-chlorophenyl)-n-butyl]imidazole,
1-[2-(4-chlorobenzyloxy)-2-methyl-4-(4-chlorophenyl)-n-butyl]imidazole, nitrate salt, m.p. 148°–149.5° C.,
1-[2-(2,4-dichlorobenzyloxy)-2-methyl-4-(4-chlorophenyl)-n-butyl]imidazole, nitrate salt, m.p. 159°–161° C.,
1-[2-(2,6-dichlorobenzyloxy)-2-methyl-4-(4-chlorophenyl)-n-butyl]imidazole,
1-[2-(4-fluorobenzyloxy)-2-methyl-4-(4-chlorophenyl)-n-butyl]imidazole,
1-[2-(2-methoxybenzyloxy)-2-methyl-4-(4-chlorophenyl)-n-butyl]imidazole,
1-[2-(4-methylbenzyloxy)-2-methyl-4-(4-chlorophenyl)-n-butyl]imidazole,
1-[2-(2-chlorobenzyloxy)-2-methyl-4-(4-fluorophenyl)-n-butyl]imidazole,
1-[2-(4-chlorobenzyloxy)-2-methyl-4-(4-fluorophenyl)-n-butyl]imidazole,
1-[2-(2,4-dichlorobenzyloxy)-2-methyl-4-(4-fluorophenyl)-n-butyl]imidazole,
1-[2-(2,5-dichlorobenzyloxy)-2-methyl-4-(4-fluorophenyl)-n-butyl]imidazole, 1-[2-(2,6-dichlorobenzyloxy)-2-methyl-4-(4-fluorophenyl)-n-butyl]imidazole,
1-[2-(3,4-dichlorobenzyloxy)-2-methyl-4-(4-fluorophenyl)-n-butyl]imidazole,
1-[2-(2-chlorobenzyloxy)-2-methyl-4-(4-bromophenyl)-n-butyl]imidazole,
1-[2-(4-chlorobenzyloxy)-2-methyl-4-(4-bromophenyl)-n-butyl]imidazole,
1-[2-(2,4-dichlorobenzyloxy)-2-methyl-4-(4-bromophenyl)-n-butyl]imidazole,
1-[2-(2,6-dichlorobenzyloxy)-2-methyl-4-(4-bromophenyl)-n-butyl]imidazole,
1-[2-(4-fluorobenzyloxy)-2-methyl-4-(4-bromophenyl)-n-butyl]imidazole,
1-[2-(2,4-dichlorobenzyloxy)-2-methyl-4-(4-methoxyphenyl)-n-butyl]imidazole.
1-[2-(2,4-dichlorobenzyloxy)-2-methyl-4-phenyl-n-butyl]imidazole,
1-[2-(2-chlorobenzyloxy)-2-methyl-4-(4-methylphenyl)-n-butyl]imidazole,
1-[2-(2-chlorobenzyloxy)-2-methyl-5-(4-chlorophenyl)-n-pentyl]imidazole,
1-[2-(4-chlorobenzyloxy)-2-methyl-5-(4-chlorophenyl)-n-pentyl]imidazole,
1-[2-(2,4-dichlorobenzyloxy)-2-methyl-5-(4-chlorophenyl)-n-pentyl]imidazole,
1-[2-(2-methoxybenzyloxy)-2-methyl-5-(4-chlorophenyl)-n-pentyl]imidazole,
1-[2-(4-methoxybenzyloxy)-2-methyl-5-(4-chlorophenyl)-n-pentyl]imidazole,
1-[2-(4-methylbenzyloxy)-2-methyl-5-(4-chlorophenyl)-n-pentyl]imidazole,
1-[2-cinnamyloxy-2-methyl-4-(4-chlorophenyl)-n-butyl]imidazole,
1-[2-cinnamylthio-2-methyl-4-(4-chlorophenyl)-n-butyl]imidazole,
1-[2-(4-chlorocinnamyloxy)-2-methyl-4-(4-fluorophenyl)-n-butyl]imidazole,
1-[2-(4-methylcinnamylthio)-2-methyl-4-(4-fluorophenyl)-n-butyl]imidazole,
1-[2-(4-phenyl-n-butylthio)-2-methyl-4-(4-fluorophenyl)-n-butyl]imidazole,
1-[2-(3-phenyl-n-propyloxy)-2-methyl-4-(4-fluorophenyl)-n-butyl]imidazole,
1-[2-(2,4-dichlorobenzyloxy)-2-methyl-4-(2,4-dichlorophenyl)-n-butyl]imidazole, nitrate salt, m.p. 171°–181° C.,
1-[2-(4-chlorobenzyloxy)-2-methyl-4-(2,4-dichlorophenyl)-n-butyl]imidazole, nitrate salt, m.p. 165.5°–166.5° C.,
1-[2-(4-chlorobenzylthio)-2-methyl-4-(2,4-dichlorophenyl)-n-butyl]imidazole, nitrate salt, m.p. 165°–167° C.,
1-[2-(2,4-dichlorophenylthio)-2-methyl-4-(2,4-dichlorophenyl)-n-butyl]imidazole, nitrate salt, m.p. 131°–132.5° C. (foaming),
1-[2-(2-chlorophenylthio)-2-methyl-4-(2,4-dichlorophenyl)-n-butyl]imidazole, nitrate salt, m.p. 109.5° C. to glass,
1-[2-(2-chlorobenzylthio)-2-methyl-4-(2,4-dichlorophenyl)-n-butyl]imidazole, nitrate salt, m.p. 114°–116.5° C.,
1-[2-(2-chlorophenoxy)-2-methyl-4-(4-chlorophenyl)-n-butyl]imidazole,
1-[2-(2,4-dichlorophenoxy)-2-methyl-4-(4-chlorophenyl)-n-butyl]imidazole,
1-[2-(3-trifluoromethyl-4-chlorophenoxy)-2-methyl-4-(4-chlorophenyl)-n-butyl]imidazole,
1-[2-(4-chlorophenoxy)-2-methyl-5-(4-chlorophenyl)-n-pentyl]imidazole,
1-[2-(2-chlorophenoxy)-2-methyl-5-(4-chlorophenyl)-n-pentyl]imidazole, and
1-[2-(4-chlorophenoxy)-2-methyl-4-(2,4-dichlorophenyl)-n-butyl]imidazole.

EXAMPLE 8

Following the procedures in Preparation 2 and Examples 1; 2; or 3, using equivalent amounts of the appropriate starting materials, there may be obtained the following compounds, which, where indicated are further characterized by conversion to the indicated acid addition salt.

1-[3-(2-chlorophenylthio)-3-methyl-5-(4-chlorophenyl)-n-pentyl]imidazole,
1-[3-(4-chlorophenylthio)-3-methyl-5-(4-chlorophenyl)-n-pentyl]imidazole,
1-[3-(2,4-dichlorophenylthio)-3-methyl-5-(4-chlorophenyl)-n-pentyl]imidazole,
1-[3-(2,5-dichlorophenylthio)-3-methyl-5-(4-chlorophenyl)-n-pentyl]imidazole,
1-[3-(2,6-dichlorophenylthio)-3-methyl-5-(4-chlorophenyl)-n-pentyl]imidazole,
1-[3-(2-bromophenylthio)-3-methyl-5-(4-chlorophenyl)-n-pentyl]imidazole,
1-[3-(2-methylphenylthio)-3-methyl-5-(4-chlorophenyl)-n-pentyl]imidazole,
1-[3-(2-chlorophenylthio)-3-methyl-5-(4-fluorophenyl)-n-pentyl]imidazole,
1-[3-(4-chlorophenylthio)-3-methyl-5-(4-fluorophenyl)-n-pentyl]imidazole,
1-[3-(2,6-dichlorophenylthio)-3-methyl-5-(4-fluorophenyl)-n-pentyl]imidazole,
1-[3-(2-chlorophenylthio)-3-methyl-4-(4-chlorophenyl)-n-butyl]imidazole,
1-[3-(4-chlorophenylthio)-3-methyl-4-(4-chlorophenyl)-n-butyl]imidazole,
1-[3-(2,4-dichlorophenylthio)-3-methyl-4-(4-chlorophenyl)-n-butyl]imidazole,
1-[3-(2,5-dichlorophenylthio)-3-methyl-4-(4-chlorophenyl)-n-butyl]imidazole,
1-[3-(2,6-dichlorophenylthio)-3-methyl-4-(4-chlorophenyl)-n-butyl]imidazole,
1-[3-(2-methoxyphenylthio)-3-methyl-4-(4-chlorophenyl)-n-butyl]imidazole,
1-[3-(2-chloro-5-methoxyphenylthio)-3-methyl-4-(4-chlorophenyl)-n-butyl]imidazole,
1-[3-(2-methoxy-5-chlorophenylthio)-3-methyl-4-(4-chlorophenyl)-n-butyl]imidazole,
1-[3-(2-chlorophenylthio)-3-methyl-4-(4-fluorophenyl)-n-butyl]imidazole,
1-[3-(4-chlorophenylthio)-3-methyl-4-(4-fluorophenyl)-n-butyl]imidazole,
1-[3-2,6-dichlorophenylthio)-3-methyl-4-(4-fluorophenyl)-n-butyl]imidazole,
1-[3-(2-chlorophenylthio)-3-methyl-4-(4-methoxyphenyl)-n-butyl]imidazole,
1-[3-(2,6-dichlorophenylthio)-3-methyl-4-(4-methoxyphenyl)-n-butyl]imidazole,
1-[3-(2,4-dichlorophenylthio)-3-methyl-4-(4-methoxyphenyl)-n-butyl]imidazole,
1-[3-(2,5-dichlorophenylthio)-3-methyl-4-(4-methoxyphenyl)-n-butyl]imidazole,
1-[3-(2-chlorobenzylthio)-3-methyl-5-(4-chlorophenyl)-n-pentyl]imidazole, 1-[3-(4-chlorobenzylthio)-3-methyl-5-(4-chlorophenyl)-n-pentyl]imidazole,
1-[3-benzylthio-3-methyl-5-(4-chlorophenyl)-n-pentyl]imidazole,
1-[3-(2-chlorobenzylthio)-3-methyl-4-(4-chlorophenyl)-n-butyl]imidazole,
1-[3-(4-chlorobenzylthio)-3-methyl-4-(4-chlorophenyl)-n-butyl]imidazole,
1-[3-(4-methylbenzylthio)-3-methyl-4-(4-chlorophenyl)-n-butyl]imidazole,
1-[3-(2-chlorobenzyloxy)-3-methyl-5-(4-chlorophenyl)-n-pentyl]imidazole,
1-[3-(4-chlorobenzyloxy)-3-methyl-5-(4-chlorophenyl)-n-pentyl]imidazole,
1-[3-(2,4-dichlorobenzyloxy)-3-methyl-5-(4-chlorophenyl)-n-pentyl]imidazole,
1-[3-(4-methoxybenzyloxy)-3-methyl-5-(4-chlorophenyl)-n-pentyl]imidazole,
1-[3-(2-chlorobenzyloxy)-3-methyl-4-(4-chlorophenyl)-n-butyl]imidazole,
1-[3-(4-chlorobenzyloxy)-3-methyl-4-(4-chlorophenyl)-n-butyl]imidazole,
1-[3-(2,4-dichlorobenzyloxy)-3-methyl-4-(4-chlorophenyl)-n-butyl]imidazole,
1-[3-cinnamyloxy-3-methyl-5-(4-chlorophenyl)-n-pentyl]-imidazole,
1-[3-(2,4-dichlorocinnamylthio)-3-methyl-5-(4-fluorophenyl)-n-pentyl]imidazole,
1-[3-(4-phenyl-n-butyloxy)-3-methyl-5-(4-fluorophenyl)-n-pentyl]imidazole,
1-[3-(3-phenyl-n-propylthio)-3-methyl-5-(4-fluorophenyl)-n-pentyl]imidazole,
1-[4-(2-fluorophenylthio)-4-ethyl-4-(4-chlorophenyl)-n-butyl]imidazole,
1-[4-(2-chlorophenylthio)-4-methyl-4-(4-fluorophenyl)-n-butyl]imidazole,
1-[4-(2-methoxyphenylthio)-4-methyl-6-(4-chlorophenyl)-n-hexyl]imidazole,
1-[3-(4-chlorophenoxy)-3-methyl-5-(4-chlorophenyl)-n-pentyl]imidazole,
1-[3-(2-chlorophenoxy)-3-methyl-5-(4-chlorophenyl)-n-pentyl]imidazole, and
1-[3-(4-chlorophenoxy)-3-methyl-5-(4-methoxyphenyl)-n-pentyl]imidazole.

EXAMPLE 9

Nitric acid (70%; d=1.42) is added dropwise to a stirred solution of 2.0g. of 1-[2-(2,4-dichlorophenylthio)-2-methyl-4-(4-chlorophenyl)-n-butyl]imidazole in 200 ml. of anhydrous ether until precipitation is complete. The product is filtered off, washed with ether, air dried, and recrystallized from acetone/ethyl acetate to yield 1-[2-(2,4-dichlorophenylthio)-2-methyl-4-(4-chlorophenyl)-n-butyl]imidazole nitrate, m.p. 126.5°–128° C.

In similar manner, all compounds of formula (I) in base form can be converted to their antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid. p-toluenesulfonic acid or salicylic acid.

EXAMPLE 10

1-[2-(2,4-Dichlorophenylthio)-2-methyl-4-(4-chlorophenyl)-n-butyl]imidazole (1.2g.) in 100 ml. of ether is stirred with excess dilute potassium carbonate solution until the salt is completely dissolved. The organic layer is then separated, washed with water, dried (MgSO$_4$) and evaporated to yield 1-[2-(2,4-dichlorophenylthio)-2-methyl-4-(4-chlorophenyl)-n-butyl]imidazole.

In similar manner, the antimicrobial acid addition salts of all compounds of formula (I) can be converted to the corresponding compounds in base form.

EXAMPLE 11

The following illustrates the preparation of representative pharmaceutical formulations which may be used for controlling fungi, bacteria and protozoa, utilizing an active compound such as a salt of 1-[2-(2-chlorophenylthio)-2-methyl-4-(4-chlorophenyl)-n-butyl]imidazole.

| A. Topical Formulation | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water      qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

| B. I.V. Formulation | |
|---|---|
| Active compound | 0.5 g. |
| Propylene glycol | 20 g. |
| Polyethylene glycol 400 | 20 g. |
| Tween 80 | 1 g. |
| 0.9 Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

| C. Oral Formation | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

I claim as my invention:
1. A compound of the formula:

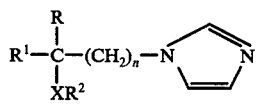

wherein R is lower alkyl; $R^1$ is 4-halo or 2,4-dihalo substituted phenethyl or phenylpropyl; $R^2$ is halo and/or methoxy substituted benzyl or phenyl; X is oxygen or sulfur; n is an integer of from 1 to 4; and the antimicrobial addition salts thereof.

2. A compound of claim 1 wherein X is sulfur.

3. A compound of claim 1 wherein X is oxygen.

4. A compound of claim 1 wherein $R^1$ is 4-halo substituted phenethyl and $R^2$ is halo and/or methoxy substituted benzyl or phenyl wherein said substitution includes a substitution in an ortho or para position.

5. A compound of claim 4 wherein n is 1.

6. The compound of claim 5 which is 1-[2-(2,5-dichlorophenylthio)-2-methyl-4-(4-fluorophenyl)-n-butyl]imidazole and the acid addition salts thereof.

7. The compound of claim 5 which is 1-[2-(2,4,6-trichlorophenylthio)-2-methyl-4-(4-fluorophenyl)-n-butyl]imidazole and the acid addition salts thereof.

8. The compound of claim 5 which is 1-[2-(2,6-dichlorophenylthio)-2-methyl-4-(4-fluorophenyl)-n-butyl]imidazole and the acid addition salts thereof.

9. The compound of claim 5 which is 1-[2-(2,4-dichlorophenylthio)-2-methyl-4-(4-fluorophenyl)-n-butyl]imidazole and the acid addition salts thereof.

10. The compound of claim 5 which is 1-[2-(2-chlorophenylthio)-2-methyl-4-(4-chlorophenyl)-n-butyl]imidazole and the acid addition salts thereof.

11. The compound of claim 5 which is 1-[2-(2,6-dichlorophenylthio)-2-methyl-4-(4-chlorophenyl)-n-butyl]imidazole and the acid addition salts thereof.

12. The compound of claim 5 which is 1-[2-(2,5-dichlorophenylthio)-2-methyl-4-(4-chlorophenyl)-n-butyl]imidazole and the acid addition salts thereof.

13. The compound of claim 5 which is 1-[2-(2,4-dichlorophenylthio)-2-methyl-4-(4-chlorophenyl)-n-butyl]imidazole and the acid addition salts thereof.

14. The compound of claim 5 which is 1-[2-(4-chlorophenylthio)-2-methyl-4-(4-chlorophenyl)-n-butyl]imidazole and the acid addition salts thereof.

15. The compound of claim 5 which is 1-[2-(2-bromophenylthio)-2-methyl-4-(4-chlorophenyl)-n-butyl]imidazole and the acid addition salts thereof.

16. The compound of claim 5 which is 1-[2-(2-methoxyphenylthio)-2-methyl-4-(4-chlorophenyl)-n-butyl]imidazole and the acid addition salts thereof.

17. A compound of claim 1 wherein $R^1$ is 2,4-dihalo substituted phenethyl and $R^2$ is 4-halo or 4-methoxy substituted benzyl or phenyl.

18. A compound of claim 17 wherein n is 1.

19. The compound of claim 18 which is 1-[2-(4-chlorophenylthio)-2-methyl-4-(2,4-dichlorophenyl)-n-butyl]imidazole and the acid addition salts thereof.

20. The compound of claim 18 which is 1-[2-(4-methoxyphenylthio)-2-methyl-4-(2,4-dichlorophenyl)-n-butyl]imidazole and the acid addition salts thereof.

21. The compound of claim 18 which is 1-[2-(4-fluorophenylthio)-2-methyl-4-(2,4-dichlorophenyl)-n-butyl]imidazole and the acid addition salts thereof.

22. The compound of claim 18 which is 1-[2-(4-bromophenylthio)-2-methyl-4-(2,4-dichlorophenyl)-n-butyl]imidazole and the acid addition salts thereof.

23. A composition useful for inhibiting the growth of fungi, bacteria or protozoa which comprises an effective amount of a compound of the formula:

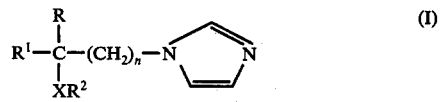

wherein R is lower alkyl; $R^1$ is 4-halo or 2,4-dihalo substituted phenethyl or phenylpropyl; $R^2$ is halo and/or methoxy substituted benzyl or phenyl; X is oxygen or sulfur; n is an integer of from 1 to 4; or an antimicrobial addition salt thereof; in admixture with a suitable carrier.

24. The composition of claim 23 suitable for pharmaceutical use wherein the carrier is a pharmaceutically acceptable, non-toxic carrier.

25. The composition of claim 24 for topical administration wherein the compound of formula I is present as between about 0.1 and 10.0 weight percent of the composition.

26. A method of inhibiting the growth of fungi, bacteria or protozoa which comprises applying to a host object containing, or subject to attach by, fungi, bacteria or protozoa, an effective amount of a compound of the formula:

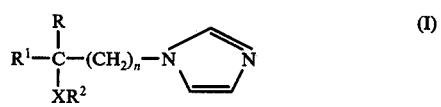

wherein R is lower alkyl; $R^1$ is 4-halo or 2,4-dihalo substituted phenethyl or phenylpropyl; $R^2$ is halo and/or methoxy substituted benzyl or phenyl; X is oxygen or sulfur; n is an integer of from 1 to 4; or an antimicrobial acid addition salt thereof, or a composition containing same as an active ingredient.

27. The method of claim 26 wherein the compound of formula I is administered topically.

28. The method of claim 26 wherein the compound of formula I is administered orally or parenterally.

* * * * *